(12) United States Patent
Graham et al.

(10) Patent No.: US 8,245,593 B2
(45) Date of Patent: Aug. 21, 2012

(54) RELEASE MECHANISM FOR ROBOTIC ARMS

(75) Inventors: Andrew Crispin Graham, Bristol (GB); Robert Oliver Buckingham, Abingdon (GB)

(73) Assignee: Oliver Crispin Robotics Limited (GB)

( * ) Notice: Subject to any disclaimer, the term of this patent is extended or adjusted under 35 U.S.C. 154(b) by 0 days.

(21) Appl. No.: 12/983,664

(22) Filed: Jan. 3, 2011

(65) Prior Publication Data

US 2011/0146441 A1     Jun. 23, 2011

Related U.S. Application Data

(63) Continuation of application No. PCT/GB2009/001656, filed on Jul. 2, 2009.

(30) Foreign Application Priority Data

Jul. 2, 2008   (GB) .................................. 0812053.7

(51) Int. Cl.
*B25J 17/02* (2006.01)
*B25J 17/00* (2006.01)
*B25J 18/00* (2006.01)

(52) U.S. Cl. ................................................. 74/490.04

(58) Field of Classification Search ........... 74/490.01, 74/490.04, 502.6; 901/21
See application file for complete search history.

(56) References Cited

U.S. PATENT DOCUMENTS

| | | | |
|---|---|---|---|
| 3,266,059 A * | 8/1966 | Stelle | 623/62 |
| 4,393,728 A | 7/1983 | Larson et al. | |
| 4,712,969 A | 12/1987 | Kimura | |
| 4,815,911 A * | 3/1989 | Bengtsson et al. | 414/7 |
| 4,848,179 A | 7/1989 | Ubhayakar | |
| 4,870,951 A | 10/1989 | Suzuki | |
| 5,179,935 A | 1/1993 | Miyagi | |
| 5,816,769 A * | 10/1998 | Bauer et al. | 414/680 |
| 6,048,307 A | 4/2000 | Gründl et al. | |
| 6,331,181 B1 | 12/2001 | Tierney et al. | |
| 6,491,701 B2 | 12/2002 | Tierney et al. | |
| 6,858,005 B2 | 2/2005 | Ohline et al. | |
| 6,866,671 B2 | 3/2005 | Tierney et al. | |
| 7,331,967 B2 | 2/2008 | Lee et al. | |
| 2002/0072736 A1 | 6/2002 | Tierney et al. | |
| 2004/0049205 A1 | 3/2004 | Lee et al. | |
| 2004/0195988 A1 | 10/2004 | Buckingham et al. | |

FOREIGN PATENT DOCUMENTS

| | | |
|---|---|---|
| DE | 4201280 C1 | 12/1992 |
| EP | 0377742 A1 | 7/1990 |
| WO | 0216995 A2 | 2/2002 |

OTHER PUBLICATIONS

International Search Report; PCT/GB2009/001656; Oct. 2, 2009; 6 pages.

* cited by examiner

*Primary Examiner* — Justin Krause
(74) *Attorney, Agent, or Firm* — St. Onge Steward Johnston & Reens LLC

(57) ABSTRACT

A robotic arm arrangement including an arm having control cables extending from the base of the arm, and coupling members for coupling the cables to actuators for linear actuation of the cables. The coupling members extend radially outwardly around the arm to enable quick release and replacement of the arm.

14 Claims, 14 Drawing Sheets

RELEASE MECHANISM FOR ROBOTIC ARMS

CROSS-REFERENCE TO RELATED APPLICATIONS

The present application is a continuation of pending International patent application PCT/GB2009/001656 filed on Jul. 2, 2009 which designates the United States and claims priority from United Kingdom patent application 0812053.7 filed on Jul. 2, 2008, the content of which is incorporated herein by reference.

FIELD OF THE INVENTION

This invention relates to robotic arms, and in particular to a release mechanism to allow for interchangeable arms.

BACKGROUND OF THE INVENTION

In the field of robotics there has been considerable development of robotic arms having a tip following capability. Such arms can carry a workload or tool and can be used for inspection and repair in confined spaces, for instance within a jet engine or the human body.

A major advance in tip following technology for robotic arms is described in our co-pending Patent Application No. WO 0216995. This application discloses a robotic arm comprising a plurality of longitudinal segments, each of which comprises one or more passive links and a control link. Control ropes or cables are provided that terminate at the control link at the end of each segment, so that by varying the length of the ropes, the arm can be caused to bend and adopt various planar or spatial shapes and configurations. This may be done for example by winding each control rope on or off a spindle using a rotary actuator or pulling the rope directly using a linear actuator. The actuators are located at the proximal end of the arm and are controlled for example by a computer control system. The ropes are generally located in the guide holes disposed towards the outer circumference of the arm.

These arms are suitable for a number of operations which may require the work head at the distal end of the arm to be at adapted or changed for the intended purpose, possibly also with appropriate changes to the control means to provide the desired operation of the arm and the work head. Interchangeable work heads are widely used. However these typically involve location of rigid elements and feed through of services, for instance power and data. Certain work heads may also require additional control ropes for motion control of the work head, which ropes must also pass through the arm. This makes exchanging a work head more complicated, such that it would be advantageous to exchange both the arm and the work head together, whilst retaining the same actuators and control and power systems. The exchangeable component at the distal end (ie the arm and work head) tends to be lower cost than the proximal system end. Furthermore other factors such as wear, or sterilisation requirements, or a change in task, may make exchange of the entire arm preferable to exchange of the work head only.

In order to do this, the exchange or release interface must enable mechanical and electrical power and electronic signals to be transferred. Furthermore the exchange process should not be time consuming, and should be straightforward in comparison with the task to be conducted by the arm. In order to provide an arm which is capable of 'tip following' along a predefined path in space in which there is little room for variance or deviation from the defined path, it is necessary to maintain the appropriate length of and tension in each control rope. In practice, due to build variance and operational effects, rope length and tension cannot be assumed. It is therefore essential that, when exchanging an arm, the control rope length and tension are managed.

Furthermore the exchange may be required mid-procedure. It will be appreciated that in such circumstances the replacement arm of the same or different design as the original arm should operate in an equivalent manner. When exchanging an arm the operating algorithm may need to be changed. An arm may have different operating characteristics or may be identical except for some specific calibration parameters that are unique to a particular arm.

Furthermore during the exchange process some actions are common to all control ropes, e.g. disengagement, and some actions of the specific to individual control ropes, e.g. tension control. It is advantageous to simplify the release and connect mechanisms, and where possible to use single mechanisms to achieve an action for multiple axes.

There is, therefore, a need for a robotic arm in which the arm is interchangeable upon a given actuator and motor assembly, where differences in hardware or function may be managed with minimal intervention from the operator, and the coordinated exchange of a number of control ropes may ensure that control rope tension and position are maintained or re-established during the process.

U.S. Pat. No. 6,866,671, U.S. Pat. No. 6,331,181 and U.S. Pat. No. 6,491,701 (Tierney) each describe a releasable tool attachment mechanism for a surgical robot. The tool uses wire ropes to transfer mechanical power from actuators through the interface to the various joints located at the tool tip. The interface also allows data to be exchanged bi-laterally. Within the tool four ropes are wound around four capstans and terminated. The releasable coupling is made between a rotating capstan and a rotating motor.

The capstan is on the tool side of the exchange, which increases the cost and bulk of the tool. Also the rope is required to wrap around the capstan which leads to increased wear and reduced control of rope length due to unequal rope tension during wrap and unwrap. Furthermore the capstans are free to rotate. This means that the mechanism can be back driven and that stored energy in the rope may cause the capstan to unwind.

U.S. Pat. No. 7,331,967 (Lee) describes a variation of Tierney in which three rope to rope connections are managed across three rotary couplings. This solution is complex with multiple rope pulleys and complex mechanisms to manage the coupling process.

Grid type end to end connections are shown in U.S. Pat. No. 6,858,005 (Ohline) which present a different technical problem. It would be expected that the actuator associated with each rope will be of larger diameter than the rope. Hence there must be means of fanning out interface connections to the actuators. One method of achieving this is to use pulleys. These pulleys must be located some distance from the release mechanism unless the release junction is able to ride around the pulleys. Wrapping ropes around pulleys will also lead to more rapid rope wear.

SUMMARY OF THE INVENTION

According to one aspect of the present invention there is provided a robotic arm arrangement comprising an elongate arm having a plurality of longitudinally extending control cables for controlling the position of the arm, a corresponding plurality of actuators for actuating the control cables, and a releasable coupling arrangement between each cable and the associated actuator, the coupling arrangement comprising a coupling member, in which each coupling member extends radially outwardly of the arm, and is arranged such that the actuators produce axial movement of the cable.

Thus the actuators may be positioned radially around the arm, and the ropes or cables may extend axially out of the end of the arm for linear motion. With this arrangement the cables may stay substantially within the arm diameter, so that the arm may be replaced more simply.

Each control cable may be equipped with an engagement member, for instance a swaged spherical ferrule, for engagement with a cooperating part associated within one end of the coupling members. Each coupling member may for example be equipped with a cup that can engage with the ferrule. The linear actuation of the control cable may thus be achieved by axial motion of the one end of the coupling members, and disengagement or reengagement may be achieved by radial motion of the one end of the coupling members.

With such an arrangement, the actuators may be provided as an 'actuator pack', in which the actuators are arranged around an aperture for receiving the proximal end of the arm. For example the arm may have an 'end of arm' plate (i.e. at the end of the working part of the arm), with the cables extending axially out of the proximal end of the end of arm plate, to form a 'cylinder' of cables where the cables are exposed, terminating at an arm base plate. The ferrules may be provided mid way along the length of the cylinder between the end of arm plate and the arm base plate. The arrangement is preferably such that when all of the ferrules are aligned at the mid-point, the arm will be straight. The distance between the plates therefore will define the 'stroke' of each cable. This length may be varied depending upon the stroke required.

The cables may be held in a co-linear position by a spring or elastic element. This also allows for preloading of the cables. For example the elastic element may be a cord which passes over a pulley in the arm base plate and returns to the end of arm plate internally of the cable. The cord may for example be about 1.5 times the length of the required stroke.

This arrangement allows for each actuator with its releasable coupling to the respective cable ferrule to be located parallel, external and radially offset with respect to each cable. In this configuration, rope bending and wear occur only within the arm. Thus cables and/or the actuators may be arranged in a concentric ring, or in a plurality of eccentric rings.

The end of arm plate and the arm base plate may be provided with locking members to engage with the structure of the actuator pack to enable precise location and transmission of forces. The arm base place may also be equipped with pins that enable electrical connection between the arm and the actuator pack. This enables bi-lateral communication of data. The control ropes may also be secured to the end of arm plate by means of a spring to ensure that each rope is under tension when disconnected.

Such arms may be hollow or include a number of hollow bores for receiving tools or services. The bores may extend from the end of arm plate to the base plate and may be accessible at the base of the device. This may allow tools and services to be simply and swiftly inserted or exchanged within the hollow bores.

Furthermore, a locking mechanism may be provided to hold the ropes in tension and to avoid the ropes becoming slack when the coupling is released. This may be particularly advantageous where a large pre-load is required. A suitable locking mechanism may secure all ropes equally; for example a drum brake with radially moving components that press against the ring of ropes. Alternatively, a sliding locking plate may be engaged and disengaged normal or perpendicular to the actuator spindles.

Furthermore sensors may be incorporated to indicate to the control means that a rope has become slack, such that the control system can make an appropriate adjustment to one or more inputs. In one example, the control system may release the tension in all the ropes and apply the appropriate tension to the segment ropes sequentially starting with the most proximal segment, to ensure correct rope tension.

A motor may be provided to disengage and reengage the coupling members with the actuators. This 'quick release' may be achieved in a number of ways. For example, the coupling members may comprise a series of pantographs operated by the motors. Alternatively, a passive spring load coupling may be provided. Decoupling may be achieved by driving the spring load couplings into the end of the arm plate, which allows the arm to be withdrawn axially.

Alternatively, the coupling members may comprise a simple offset plate equipped with a mechanical quick release arrangement. In this embodiment the control cable actuators may be mounted in line with the straight arm with a radial offset. The coupling member between the actuator and cable may be an offset plate. Each cable may be equipped with a ferrule and each offset plate may have a corresponding component which can engage with the ferrule. The engagement may be arranged such that by driving all of the actuators and offset plates to an end stop, the engagement means releases the rope ferrule.

It will be appreciated that creating a sterile boundary between the arm and the environment (e.g. the human body) may be important. The most proximal arm link may be securely fixed to the end of arm plate, and may be designed and locate with the actuator mechanism housing in a way to provide a sterile boundary. However it will be appreciated that the control ropes must pass through the link creating a need for a sterile boundary between a sliding wire rope and guide hole. The link may be equipped with a series of brushes or air jets. Furthermore the cable guide holes through the end of arm plate may be equipped with reservoirs that may be filled with lubricant for acting as a barrier to ingress the egress of material. If the link is made adequately long compared with the stroke of each rope then each rope may be coated with a wax or grease which will tend to remain within the link. This fluid barrier may remain in place for the life of the arm or may be replenished at intervals.

The arm may also be equipped with a protective skin or sleeve such that the complete arm remains within the sterile boundary. This sleeve may engage with just the end link or may engage with both end link and the actuator pack or just the actuator pack. It will be appreciated that the same concerns arise for an interchangeable rope controlled end of arm work head, and similar structures may be applied there.

In a particular aspect of the invention, the arm may also incorporate data relating to the nature and state of the arm, its prior use, the way in which it is to be controlled, and the intended purpose of the arm and the manipulation of work piece at the distal end thereof. The calibration and the control algorithms for the arm, therefore, may be incorporated in the arm and may be read from the arm by the control program. For example, different lengths of arm may be applied each with different motor control characteristics. The motor drive means may have a large plurality of motors incorporated therein not all of which may be arranged for connection to an appropriate control rope. In this way, therefore, a drive assembly generally arranged for a five segment arm, say, can equally well be employed to drive a three segment arm.

In another aspect, the invention provides a robotic arm arrangement comprising an elongate arm having a plurality of longitudinally extending control cables for controlling the position of the arm, a corresponding plurality of movable actuators for actuating the control cables, a locking mechanism for locking the actuators against movement, a corresponding plurality of drive elements for driving movement of the actuators, and a releasable coupling arrangement between each actuator and each drive element.

BRIEF DESCRIPTION OF THE DRAWINGS

In order that the invention may be more readily understood, reference will now be made, by way of example, to the accompanying drawings, in which.

DETAILED DESCRIPTION OF THE INVENTION

Figure 1:
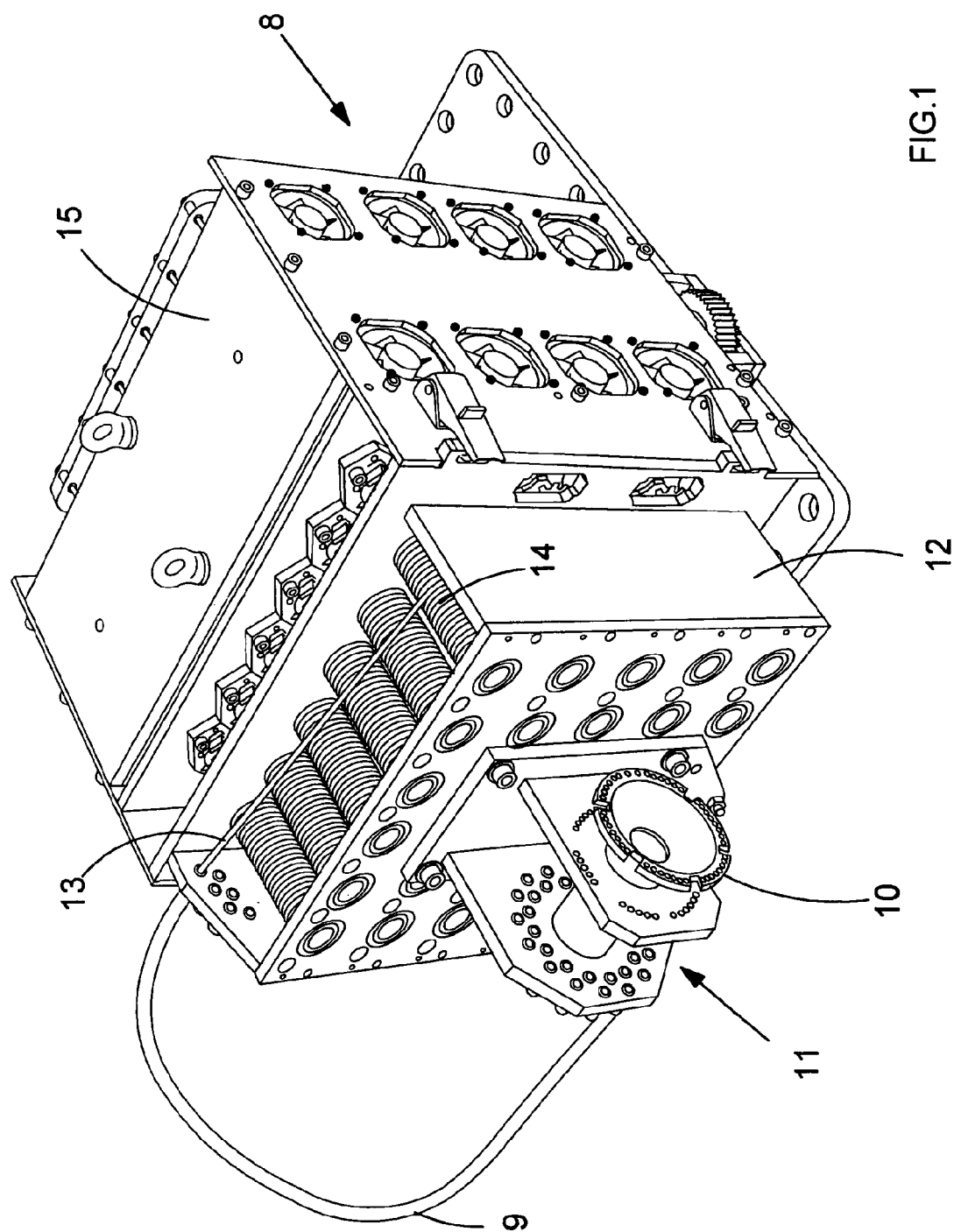
FIG. 1 is a diagrammatic perspective view of a robotic arm arrangement according to one embodiment of the present invention.

Referring to FIG. 1, a base plate 10 of a robot arm is attached via an arm mount 11 to an arm actuator pack 12. The robot arm (not shown) is of the type comprising a plurality of articulated links and control cables or ropes extending from the base plate to terminate at various control links for controlling the shape of the arm. Each control rope 13 is wrapped around a spindle 14 of each actuator and passes through a Bowden Sleeve to the arm mount. (Only one control rope is shown for ease of description.) A drive pack 15 comprises thirty motors that drive the thirty spindles through quick release couplings, as described in more detail below.

Figure 2:
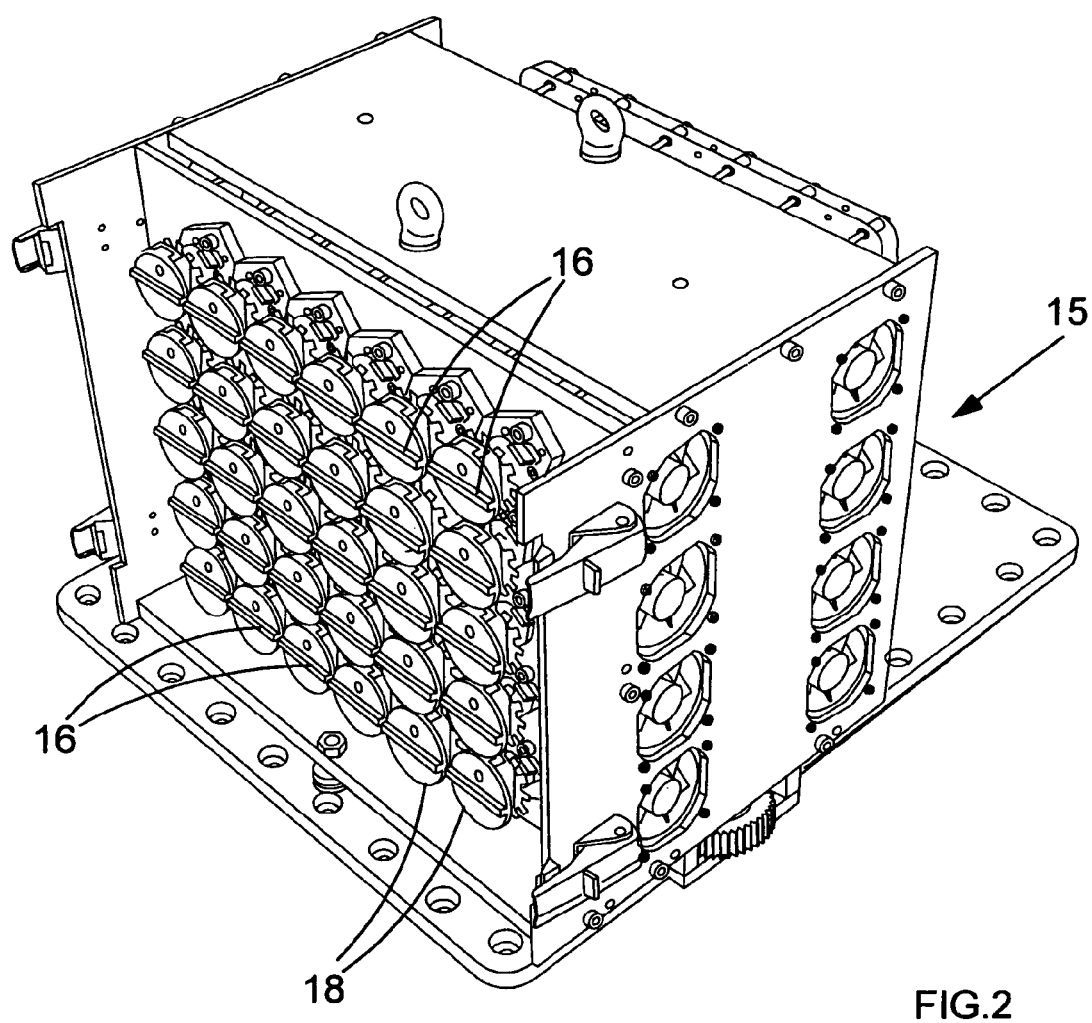
FIG. 2 is a diagrammatic perspective view of the drive arrangement of the arm of FIG. 1.

Referring to FIG. 2 the drive pack 15 is shown without the actuator pack. The drive elements each have a drive coupling 18 comprising a disc having a protruding ridge 16, which are shown aligned horizontally.

Figure 3:
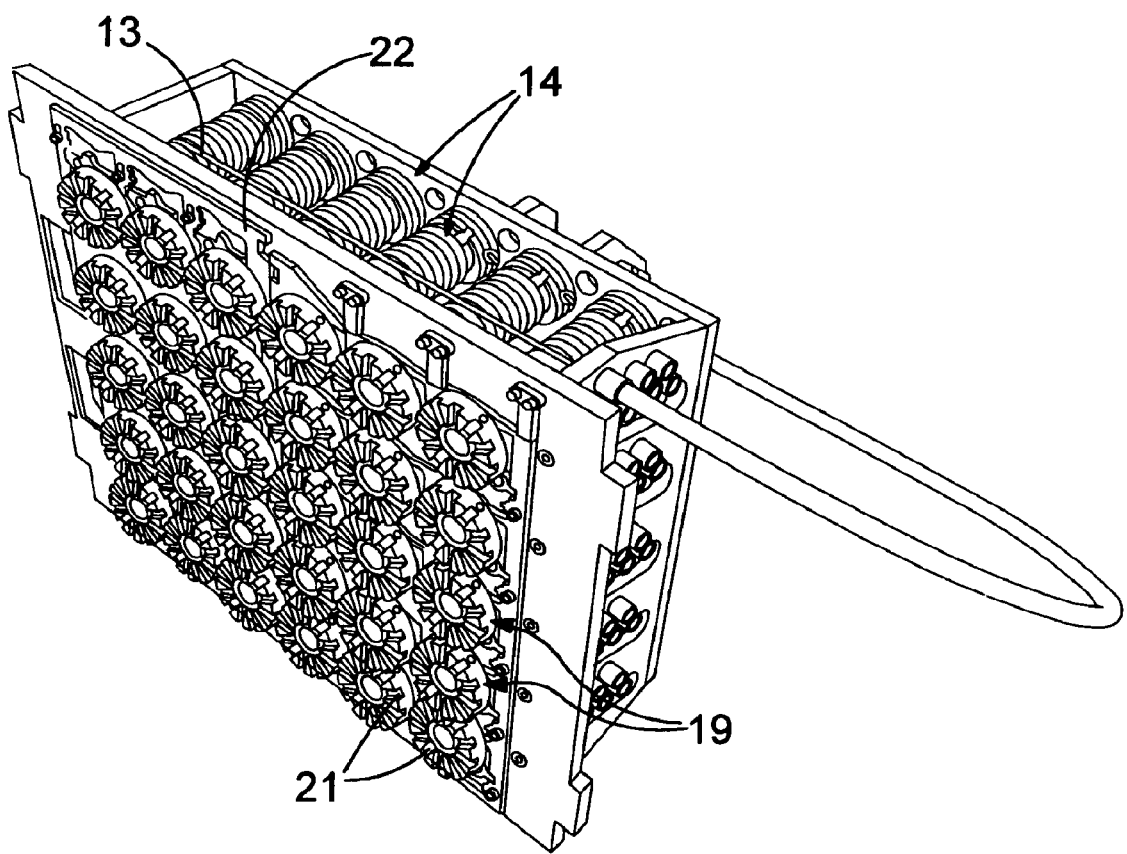
FIG. 3 is a diagram of the actuator arrangement of FIG. 1.

Referring to FIG. 3 the actuator pack contains thirty spindles 14 onto which the control cables 13 are wound. The rotational position of each spindle controls the deployed length of each cable; the length of each cable controls the arm shape. Each spindle has an actuator coupling 19 comprising a disc having a plurality of depressions 21 which are sized to receive the ridges 16 of the drive couplings 18. The actuator couplings 19 are attached to the spindles and angularly fixed thereto by means of a key and keyway. Each actuator coupling 19 is shaped so as to interface to the drive couplings 18 on the drive pack to link the angular position of each spindle to the angular position of the associated drive element or motor.

The spindle box assembly includes a locking mechanism including plates 22 which allow the angular rotation of each spindle to be locked in a specific position. This enables the removal of the actuator pack and arm from the drive pack without loss of control or knowledge of the angular rotational position of each spindle. Thus, an arm may be detached from the drive pack and later re-attached to the drive pack without the need for re-initialisation of the arm.

A useful feature of this arrangement of the quick release mechanism is that it allows the spindle box and, by association, the arm, to be attached to the actuator pack in one of two possible orientations. These orientations would be termed left- and right-handed configurations in common robotics parlance. This property derives from the existence of an axis of revolute symmetry (at the quick release interface), which is located in the centre of the spindle box and in the centre of the actuator pack.

Figure 4:
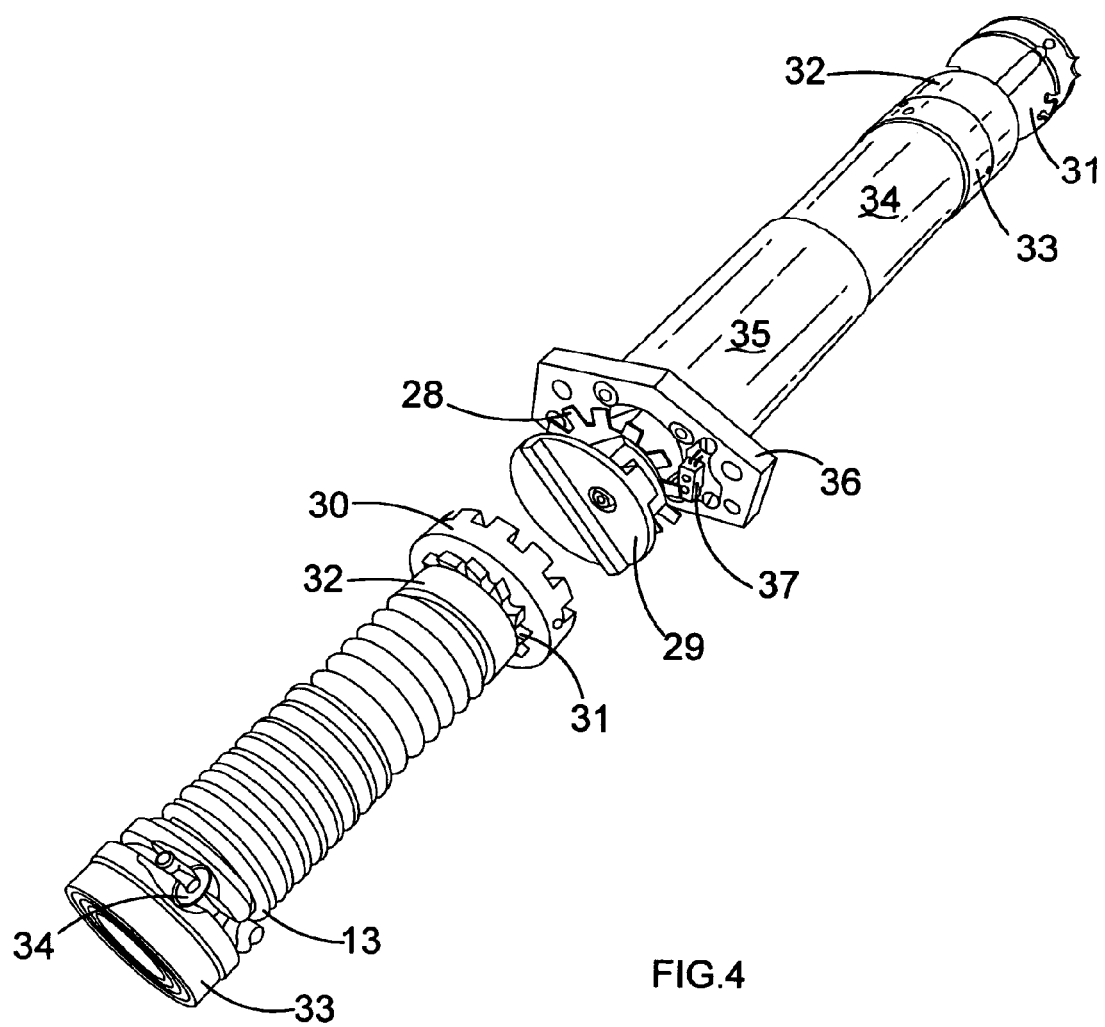
FIG. 4 is a diagram of a rotary coupling of the arrangement of FIG. 1.
Figure 5:
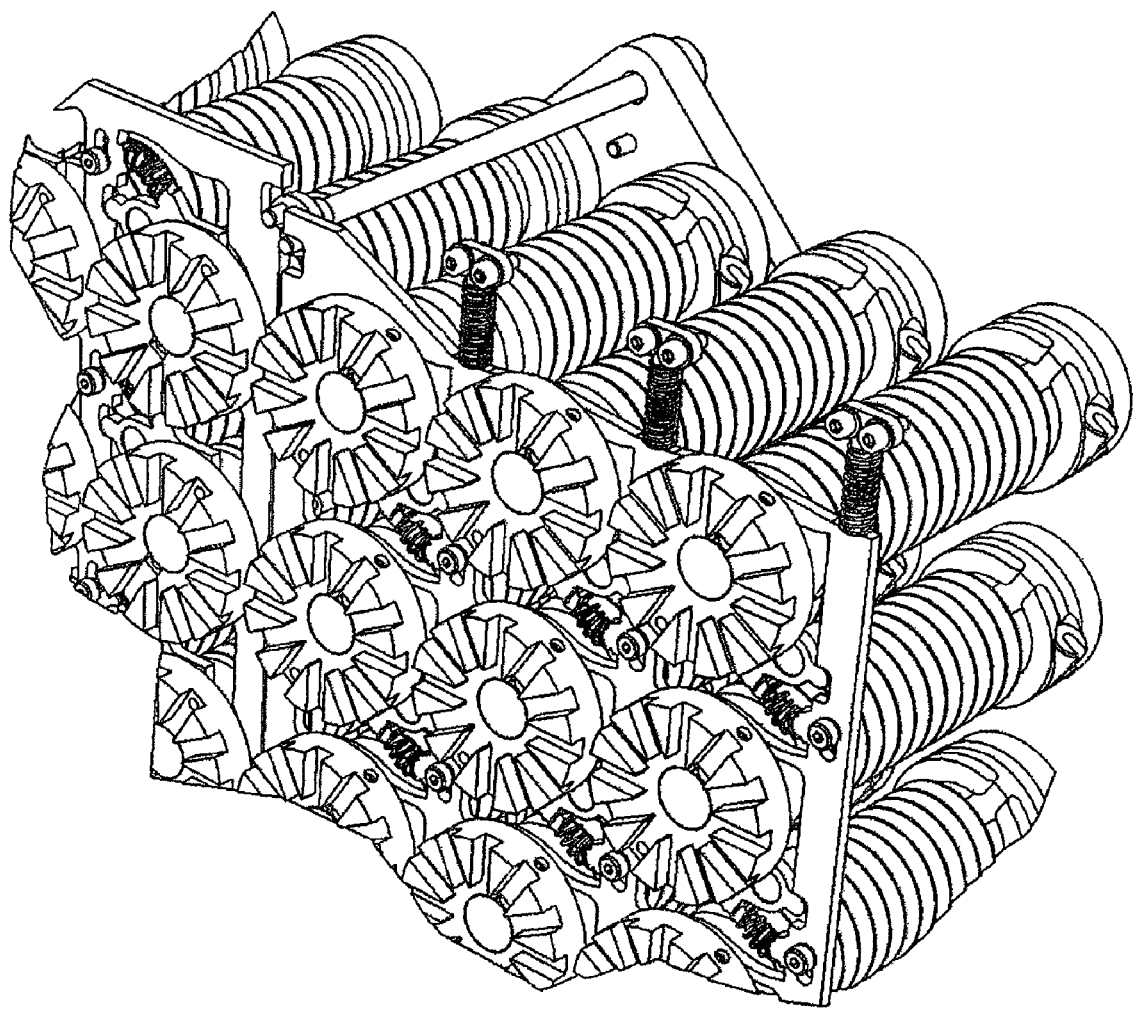
FIG. 5 is a diagram of a locking mechanism for the actuators in arrangement of FIG. 1.

FIG. 4 shows in more detail the drive, actuator and coupling assembly for a single cable. The assembly comprises a controller 31, an encoder 32, a brake 33, a motor 34, a gearbox 35, a mounting plate 36, an initialisation sensor 37 and rotary flag 28, a drive coupling 29, an actuator coupling 30, a ratchet 31, bearings 32, 33, a control rope 13 and a control rope grip 34.

The drive coupling part is mounted on the gearbox output shaft. A toothed sensor flag is supported on the drive coupling part. The mounting plate includes location features for a reflective opto-switch. This switch, in combination with the sensor flag, is used to enable the controller to sense when the gearbox output shaft is suitably oriented to enable the drive coupling part to engage with the actuator coupling part mounted on the spindle assembly.

The spindle is fitted with an actuator coupling part (which interfaces to the drive coupling part of the assembly). The actuator coupling part is slotted in a number of positions, in this case, 6 slots each at 30 degrees to the next, allowing 12 positions of coupling with respect to the drive coupling part, or 30 degrees between possible coupling orientations. The angle between adjacent slots must be small enough so that the spindle can be rotated to the nearest available slot without excessively deforming the arm. In this case, it was determined that 30 degrees between slots was adequate, given the size and flexibility of the arm and the elasticity of the system elements, most particularly the rope itself.

The number of ratchet teeth is the same as the number of slots. The ratchet forms part of the locking mechanism (described in more detail below), the intention being that, regardless of which ratchet tooth is held in the locking mechanism, the front face of the actuator coupling appears to offer the same interface features to the drive coupling part.

Figure 6A:
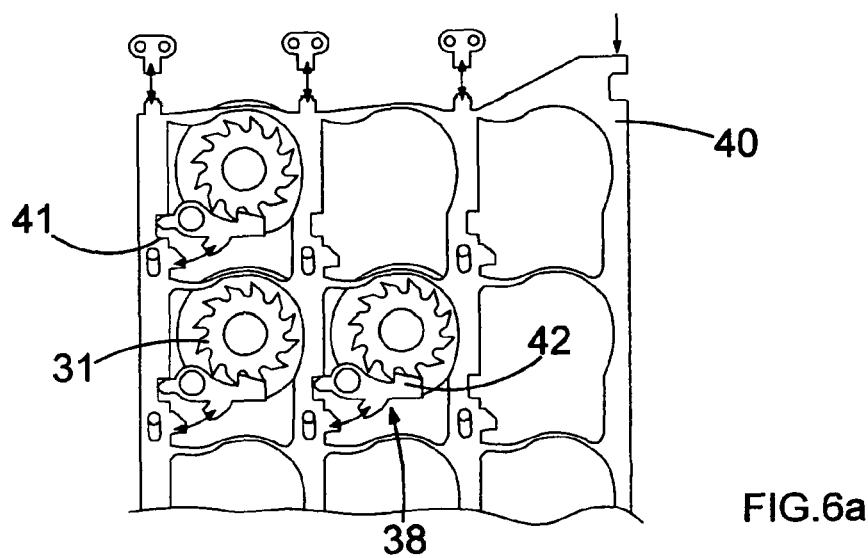
FIGS. 6a to 6c are a sequence of diagrams showing the locking mechanism action.
Figure 6B:
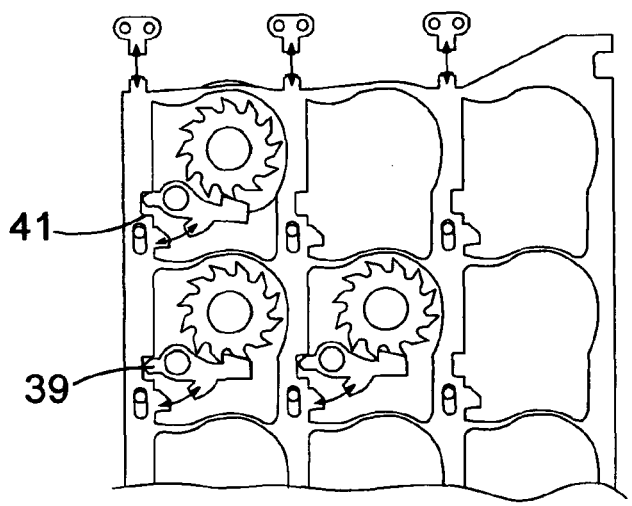
Figure 6C:
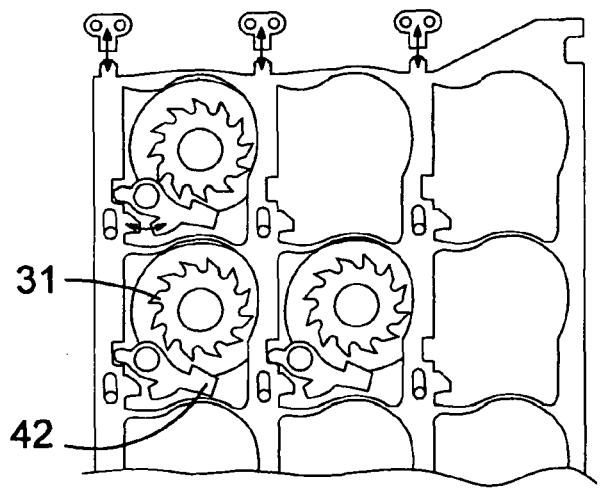

Referring to FIG. 6, the locking mechanism for a set of spindles is controlled by movement of a slide plate 40. In FIG. 6a the ratchets 31 are locked by engagement of the ratchet teeth with latches 42 provided on the end of pawls 38. When the plate 40 moves upwardly, as shown in FIGS. 6b and 6c, the tail 39 of each pawl 38 is pushed up by the lower surface of each corresponding indent 41 in the plate 40 which receives the tail. Thus the latches 42 move downwardly releasing the ratchets 31 and allowing the spindles to rotate.

In this example, the slide plate is one of two slide plates which are, in turn, operated by a crank. Thus, all 30 spindles may be locked by one operating member (i.e. the crank). The symmetrical arrangement of two slide plates may also enable automatic operation of the slide plates by a single electric actuator. The symmetry matches the symmetry of the spindle pack as a whole, enabling "right-handed" and "left-handed" installations of the spindle box on the actuator pack. The arrangement allows the state of the locking mechanism, which comprises a set of spindle locks, to be determined by two switches.

The capacity to sense the state of the locking mechanism allows an automatic controller (e.g. a computer and software) to control the process of locking or unlocking the spindles. Thus, an operator may request that the controller locks or unlocks the spindles and the controller can detect whether the process is complete or still under way.

Figure 7:
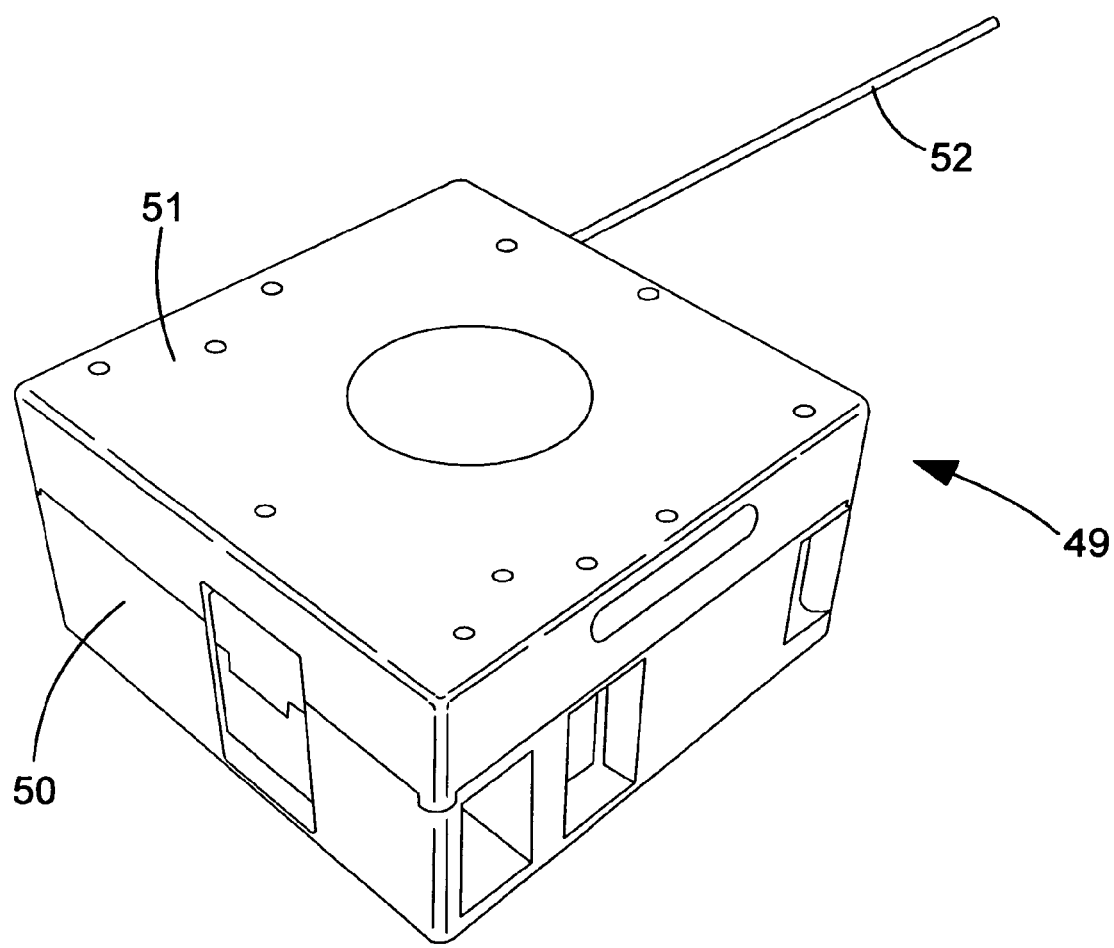
FIG. 7 is a diagrammatic view of an arm arrangement according to another embodiment of the present invention.

Referring to FIG. 7 another embodiment is shown in which an actuator pack 51 and drive pack 50 are connected together within a housing 49. The arm 52 is stowed within the actuator pack and is advanced out of the actuator pack or retracted into the actuator pack by means of the drive elements located in the drive pack.

Figure 8:
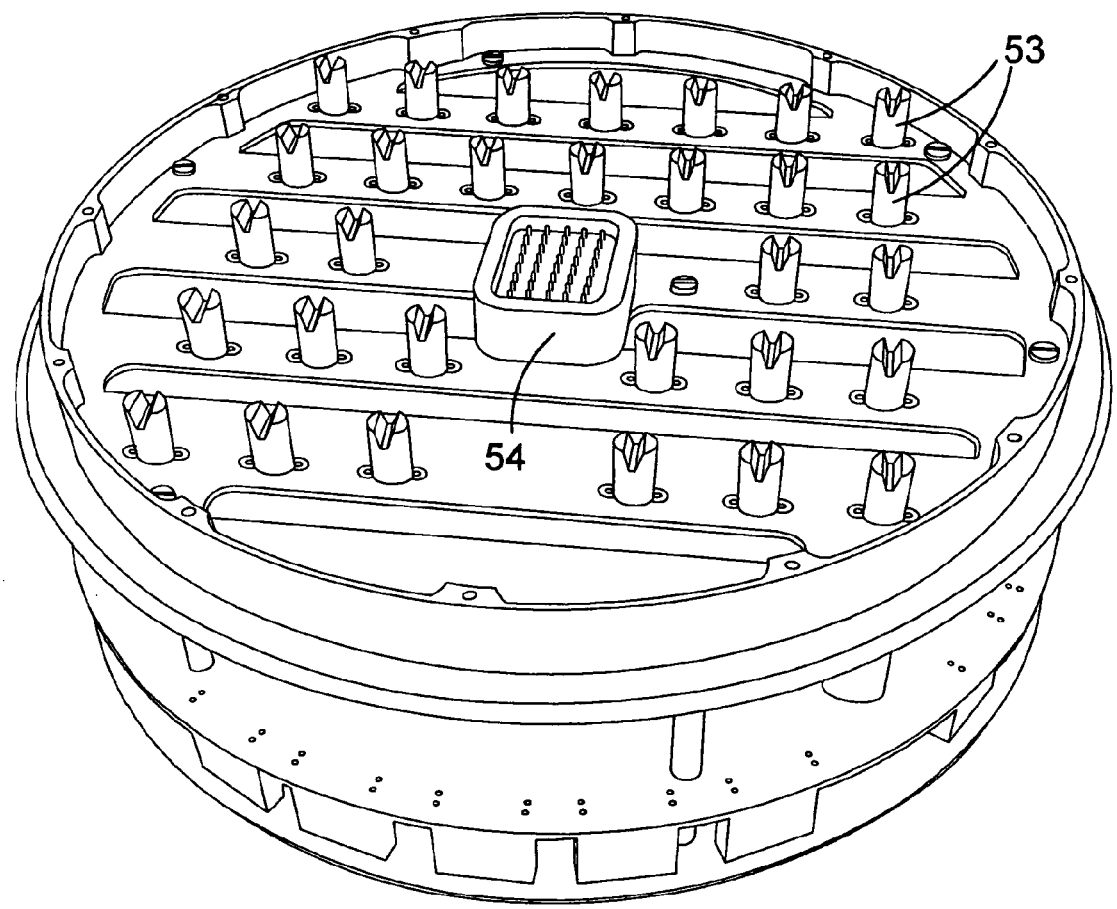
FIG. 8 is a diagram of a drive arrangement of the arm of FIG. 7.
Figure 9:
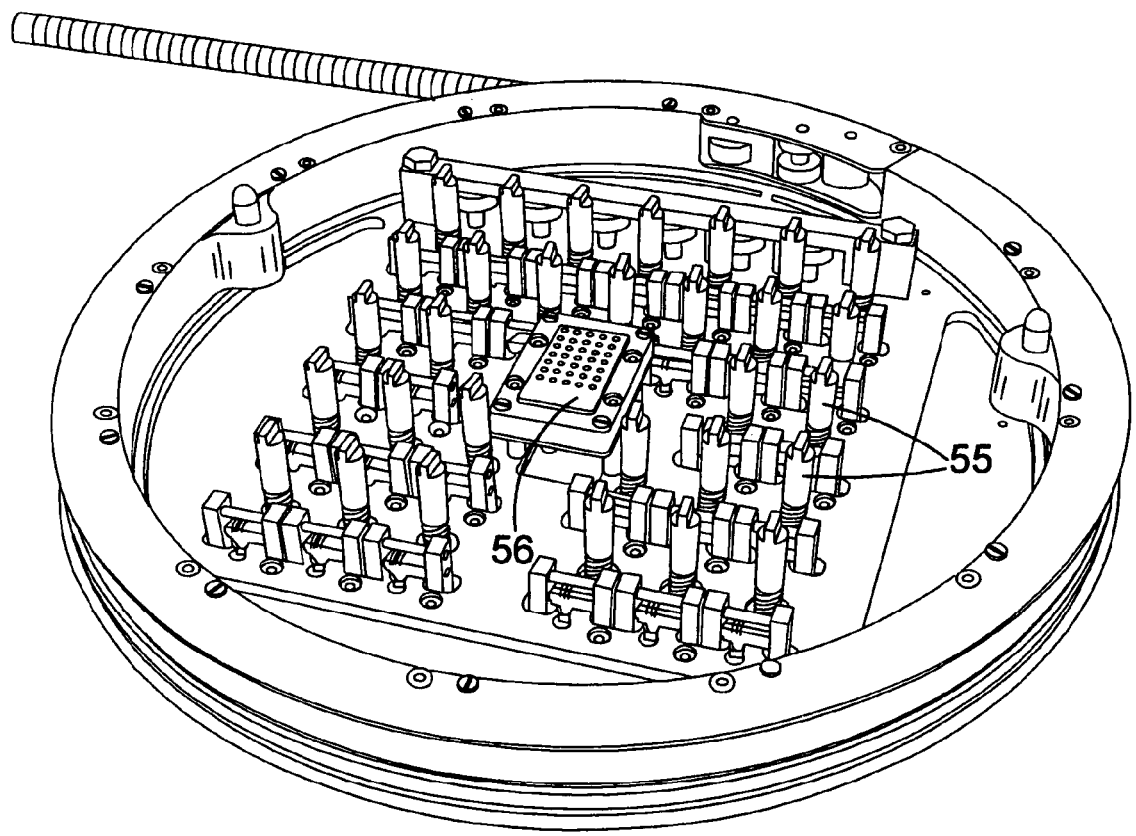
FIG. 9 is a diagram of an actuator arrangement for the arm of FIG. 7.

Referring to FIG. 8, an array of drive couplings 53 is shown, along with a spring pin 54 for making electrical connections between the actuator pack and drive pack. Referring to FIG. 9 an array of actuator couplings 55 of the actuator pack is shown with a corresponding electrical connector 56. The actuator couplings are mounted on springs such that they may only engage with the drive coupling when the drive coupling is correctly aligned. The alignment method is to rotate each motor by a maximum of one half turn.

Figure 10:
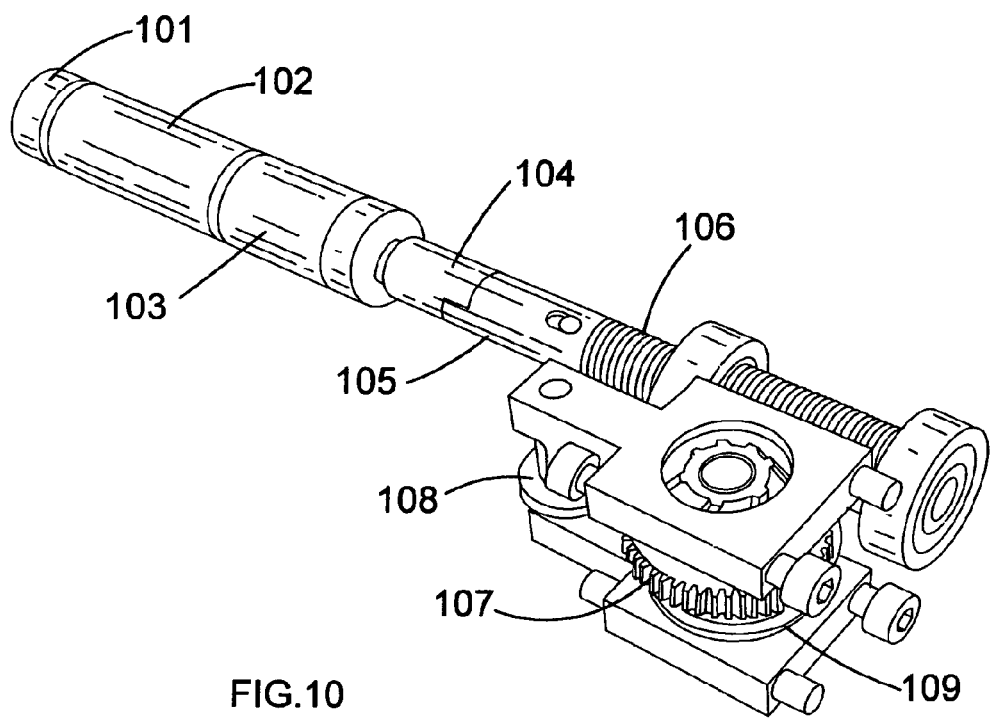
FIG. 10 is a diagram of a rotary coupling for the arm of FIG. 7.

Referring to FIG. 10 the arrangement for a single cable is shown in more detail. The arrangement comprises an encoder 101, a motor 102, a gearbox 103, a drive coupling 104, an actuator coupling 105, a spring 106, a gear 107, a spindle 108, and a pulley 109. The control rope is not shown. The control rope is secured to the spindle and follows a path to the pulley block shown in FIG. 9 at the base of the arm before passing up through the arm.

Figure 11:
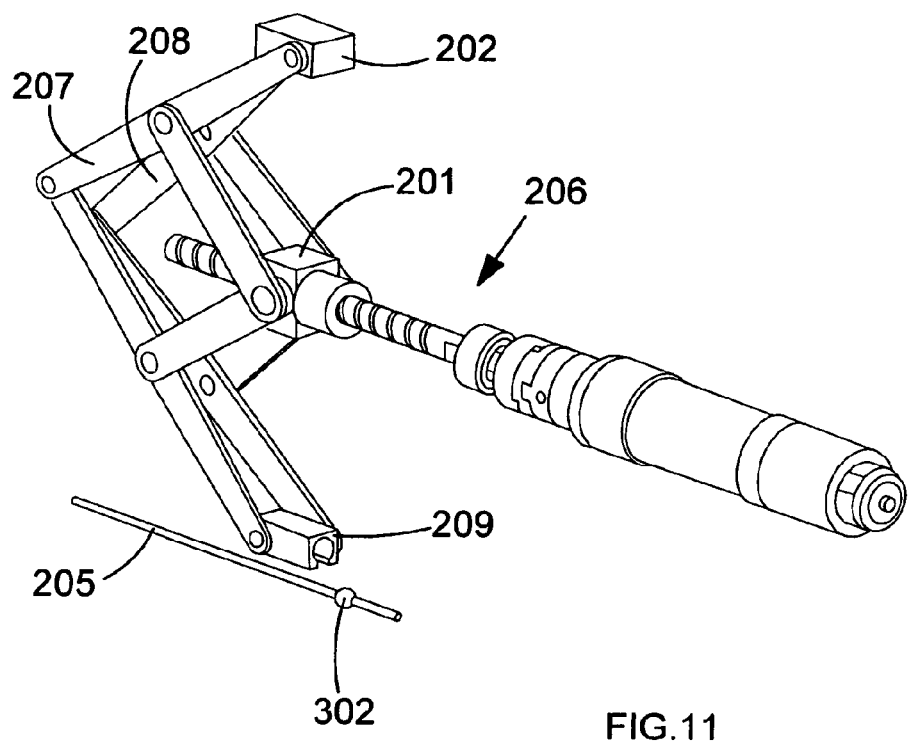
FIG. 11 is a diagrammatic perspective view of a coupling arrangement for an arm according to a further embodiment of the present invention.
Figure 12:
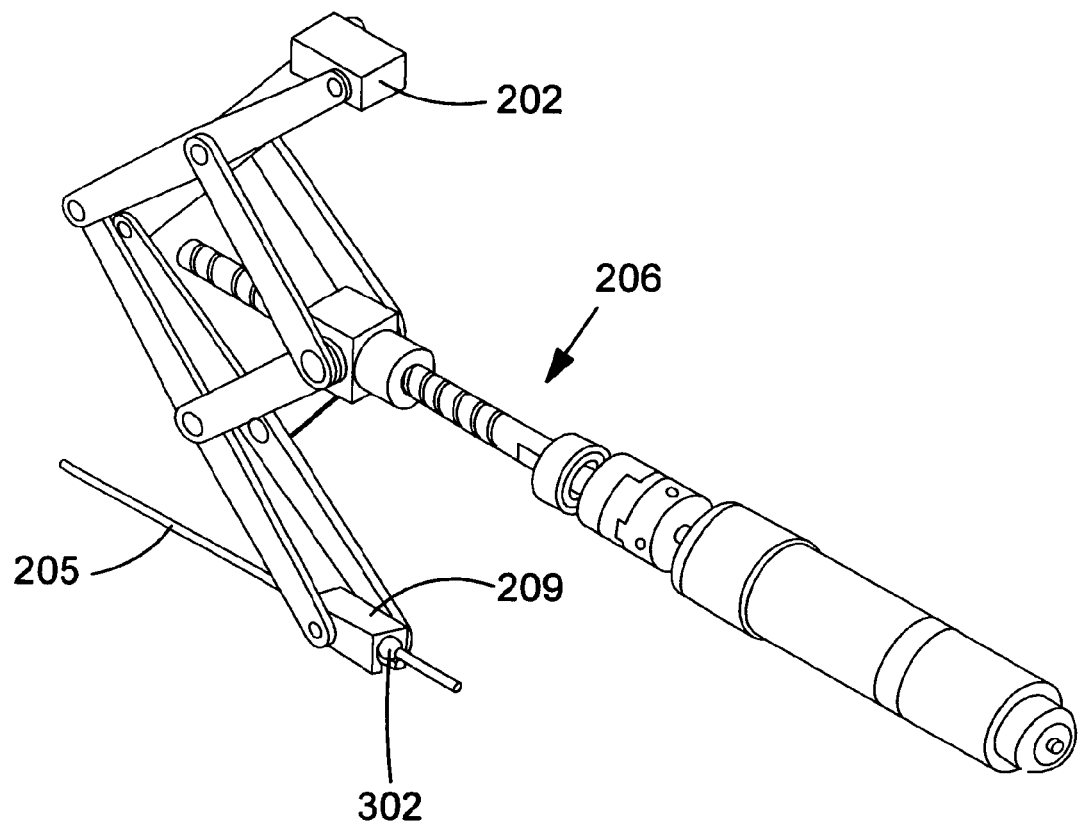
FIG. 12 is a further diagrammatic view of the coupling of FIG. 11.
Figure 16:
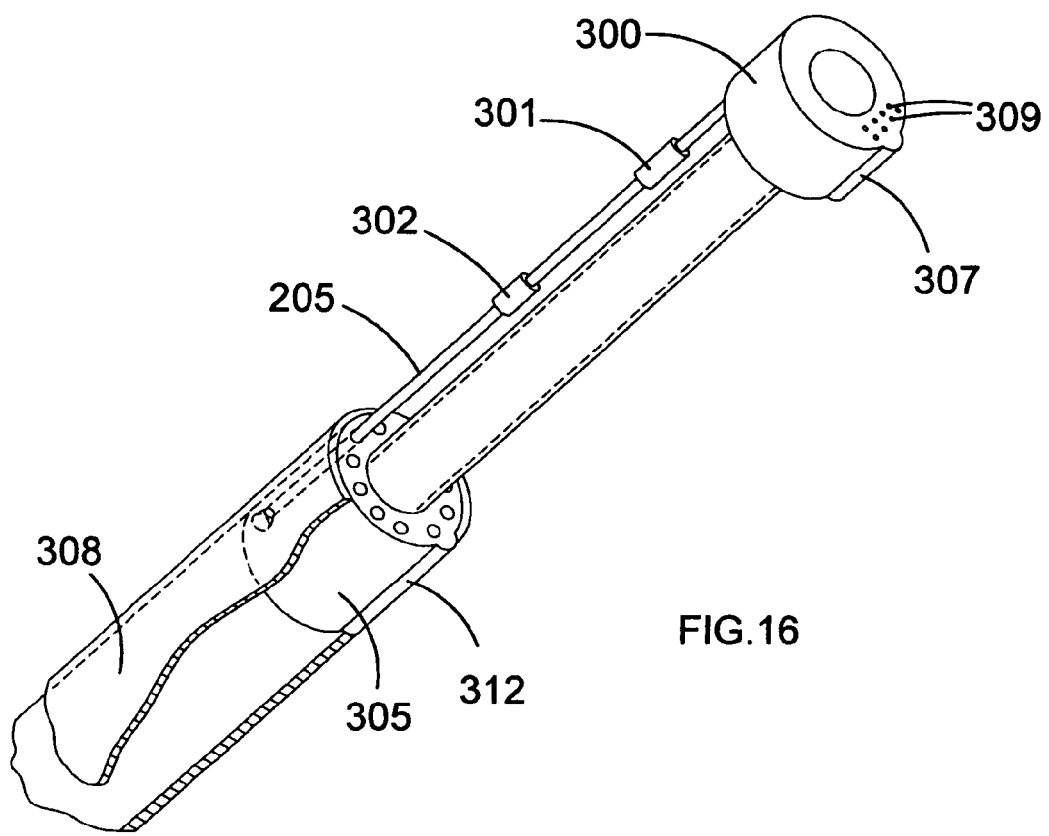
FIGS. 16, 17 and 18 show the proximal end of the arm for use with the couplings shown in FIGS. 11 to 15.

Referring to FIG. 11 another embodiment is shown in which the actuation is by linear movement of the control ropes. A ferrule 302 is attached to each control rope 205 near the proximal end of the control rope. The proximal end of the control rope is secured to an arm base plate 300 through a spring 301, as shown in FIG. 16. The spring is used to ensure that the ropes do not become slack in any arm configuration. The spring also holds the section of rope between the base plate 300 and the base of the arm straight on a known line.

The arm is controlled by many control ropes 205. The actuator pack comprises a number of linear actuators one for each control rope. Each linear actuator 206 is connected to a pantograph mechanism comprising two pantographs. Each pantograph has two inputs 201,202 and one output 203. The outputs from each pantograph are connected to a cup 209 which engages with the ferrule 302 secured to the control rope. Each linear actuator is shown connected to the central inputs 201 of the pantograph. The other inputs 202 are connected to the quick release column. The linear actuator 206 is used to pull the control rope 205. The input 202 is connected to a quick release column. For simplification only one actuator is shown.

By moving the quick release column down the output will move the cup down and allow the cup to disengage from the ferrule. Engagement is achieved by reversing this process.

It will be appreciated that a single pantograph can be used although a different motion will be achieved.

FIG. 16 shows the arm base plate 300 and the end of arm link 305. The end plate may have an engagement feature 307 for locating with an engagement feature in the actuator pack. The end of arm link may also have an engagement feature 312 for locating within a socket in the actuator pack housing. A skin or sleeve 308 secured to the arm may engage with the actuator pack housing at the arm socket providing a sterile boundary.

Figure 13:
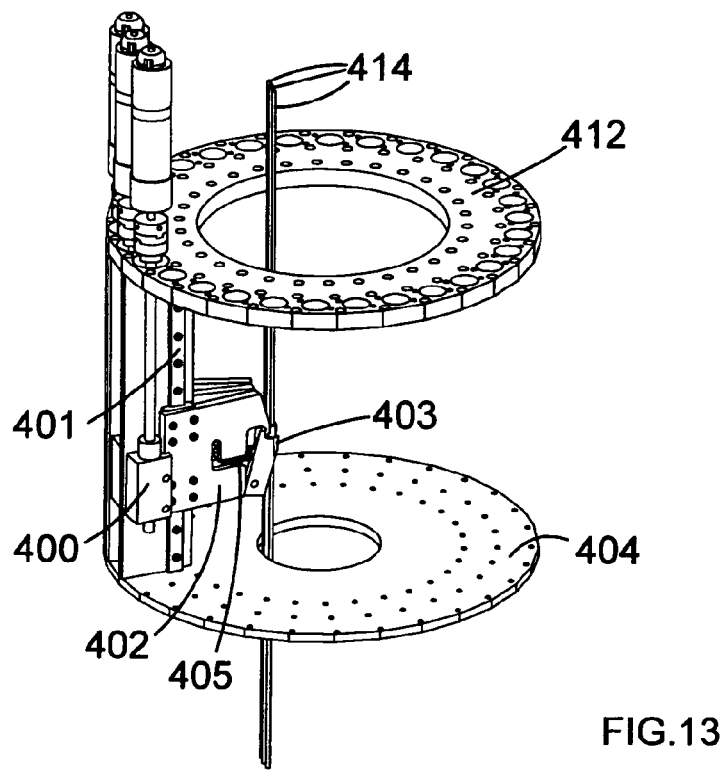
FIG. 13 is a diagrammatic perspective view of a coupling arrangement according to an alternative embodiment of the present invention.

Referring to FIG. 13, in an alternative coupling arrangement, a linear rope actuator 400 is mounted on a linear slide 401. A radially extending offset plate 402 is attached to the actuator and is equipped with a rope engagement plate 403. The engagement plate for engaging a ferrule 413 on the rope 414 includes a spring 405 which biases the engagement plate inwardly towards the rope. Only three actuators, offset plates and engagement plates are shown for clarity.

Figure 14:
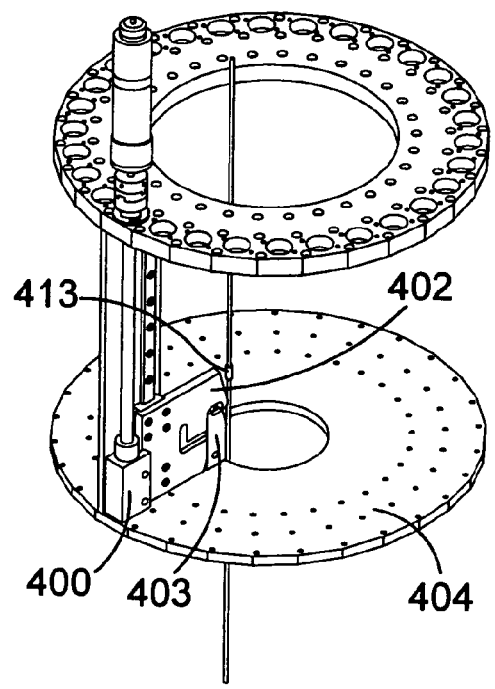
FIG. 14 is a further diagram showing the coupling of FIG. 13.
Figure 15:
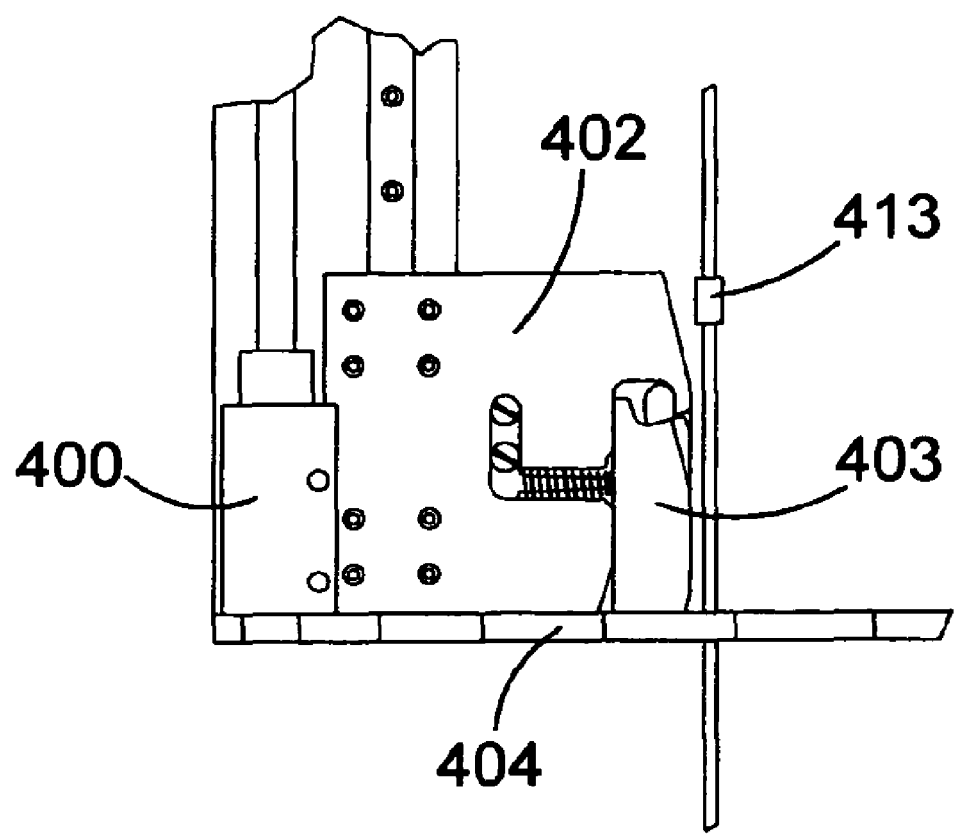
FIG. 15 is a more detailed view of the coupling of FIG. 13.

When the actuator is driven to its full extent, as shown in FIG. 14 and FIG. 15, contact with an end stop plate 404 causes the engagement plate 403 to pivot and retract to release the control rope ferrule 413. The end stop may also be used as a physical datum for initialising the actuators.

Figure 18:
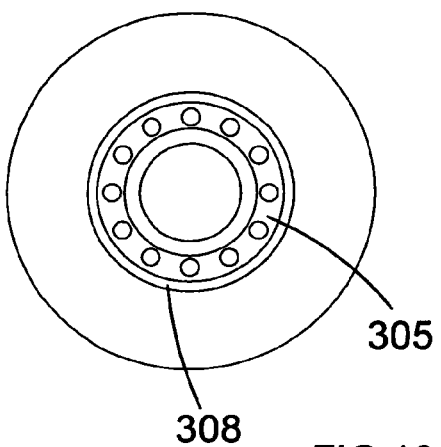

Referring to FIGS. 16 and 18 tension is maintained in the control ropes by means of the spring 301, which avoids wires becoming slack and ensures that the ropes are aligned with the engagement member of the actuator. The arm is equipped with an end of arm link 305 which engages with the end stop plate 404. A sterile boundary may be created by securing the sleeve 308 to the end stop plate. The end of arm plate 300 may be equipped with electrical connectors 309 for power and data and electronics to store information within the arm.

Figure 17:
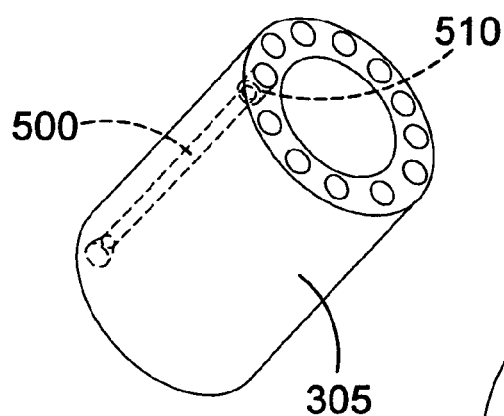

Referring to FIG. 17 the end of arm link 305 may be long enough such that the holes 500 through the end of arm link can be made long enough so that when filled with a viscous fluid the fluid will tend to remain within the hole in order to provide a seal. The holes may include features 510 to act as reservoirs for the viscous fluid.

What is claimed is:

1. A robotic arm arrangement comprises an elongate robotic arm having a plurality of control cables extending along the arm for controlling the position of the arm, a corresponding plurality of actuators for actuating the control cables, and a releasable coupling arrangement between each cable and the associated actuator, the releasable coupling arrangement comprising a coupling member, in which the coupling member extends radially outwardly with respect to the arm, and is arranged such that the actuators produce axial movement of the cables, and wherein the cables extend axially out of an end of arm plate provided at a proximal end of the arm, and terminate at an arm base plate, with ferrules being provided between the end of arm plate and the arm base plate.

2. A robotic arm arrangement according to claim 1, in which the actuators are positioned radially around the arm.

3. A robotic arm arrangement according to claim 1, in which each control cable comprises an engagement member for engagement with a cooperating part associated within one end of the coupling members.

4. A robotic arm arrangement according to claim 3 in which the engagement member is one of the ferrules, and the cooperating part is a cup.

5. A robotic arm arrangement according to claim 1 arranged such that linear actuation of the control cable is achieved by axial motion of one end of the coupling members, and disengagement or reengagement is achieved by radial motion of the one end of the coupling members.

6. A robotic arm arrangement according to claim 1, in which the actuators are provided in a housing and are arranged around an aperture in the housing for receiving the proximal end of the arm.

7. A robotic arm arrangement according to claim 1 in which the cables are held in co-linear position by a spring or elastic element.

8. A robotic arm arrangement according to claim 1 in which the elastic element is a cord which passes over a pulley in the arm base plate and returns to the end of arm plate internally of the cable.

9. A robotic arm arrangement according to claim 1, in which the end of arm plate and the arm base plate are provided with locking members to engage with an actuator housing.

10. A robotic arm arrangement according to claim 1, in which the arm base plate is provided with electrical contacts for electrical connection between the arm and the actuators for communication data.

11. A robotic arm arrangement according to claim 1, in which the control cables are secured to the end of arm plate by means of a biasing member for holding each control cable under tension when disconnected.

12. A robotic arm arrangement according to claim 1, in which the arm comprises a plurality of hollow bores for receiving tools or services, the hollow bores extending from the end of arm plate to the arm base plate and being accessible at a base of the arrangement.

13. A robotic arm arrangement comprises an elongate robotic arm having a plurality of control cables extending along the arm for controlling the position of the arm, a corresponding plurality of actuators for actuating the control cables, and a releasable coupling arrangement between each cable and the associated actuator, the releasable coupling arrangement comprising a coupling member, in which the coupling member extends radially outwardly with respect to the arm, and is arranged such that the actuators produce axial movement of the cables, and wherein the robotic arm arrangement comprises a locking mechanism arranged to hold the control cables in tension after disengagement from the actuators, the locking mechanism being operable to secure all cables.

14. A robotic arm arrangement according to claim 1, in which the coupling members comprise a plurality of pantographs, or a passive spring load coupling.

* * * * *